United States Patent [19]

Holmström

[11] Patent Number: 4,707,860

[45] Date of Patent: Nov. 24, 1987

[54] WELDING SHIELD

[76] Inventor: Per-Olof Holmström, Wälluf 40, Påarp, Sweden, S-260 33

[21] Appl. No.: 674,401

[22] Filed: Nov. 21, 1984

[63] Continuation of PCT SE84/00103, Mar. 22, 1984, published as WO84/03621, Sep. 27, 1984

[30] Foreign Application Priority Data

Mar. 24, 1983 [SE] Sweden ............................. 83016253

[51] Int. Cl.⁴ ............................................. A61F 9/06
[52] U.S. Cl. ......................................................... 2/8
[58] Field of Search .................... 2/8, 432, 9; 219/147

[56] References Cited

U.S. PATENT DOCUMENTS

| | | | |
|---|---|---|---|
| 3,112,490 | 12/1963 | Malcom, Jr. | 2/8 |
| 3,231,896 | 2/1966 | Henderson | 2/8 |
| 3,521,629 | 7/1970 | Reynolds | 2/8 X |
| 3,756,692 | 9/1973 | Scott | 219/147 X |
| 3,868,727 | 3/1975 | Paschall | 2/8 |
| 4,155,122 | 5/1979 | Budmiger | 2/8 |

FOREIGN PATENT DOCUMENTS

| | | | |
|---|---|---|---|
| 1121192 | 4/1982 | Canada | 2/8 |
| 0652943 | 3/1979 | U.S.S.R. | 2/8 |

Primary Examiner—Peter Nerbun
Attorney, Agent, or Firm—Merchant, Gould, Smith, Edell, Welter & Schmidt

[57] ABSTRACT

Welding shield adapted to be positioned in front of the face of the welder for protection radiation. Said shield comprises a transparent dark welding glass (17) which is arranged as a locally limited portion to be positioned in front of the eyes. Around this welding glass there is provided a transparent portion which is highly light-reflecting and UV-absorbing and comprises a planar panel (13) with the welding glass attached to it.

8 Claims, 5 Drawing Figures

WELDING SHIELD

This is a continuation of application Ser. No. PCT/SE84/00103, filed Mar. 22, 1984.

The invention relates to a welding shield which is intended to be positioned in front of the welder's face so as to give protection against harmful radiation, said welding shield comprising a dark welding glass.

In order to provide protection against the harmful radiation from an electric welding arc it is necessary that the welding glass is very dark, which means that the welding glass allows observation of the arc through the welding glass during welding without discomfort and without injuries to the eyes. However, there is no possibility of looking through the welding glass sufficiently clearly when the arc is extinguished e.g. in order to ignite the electrode, knock off slag, inspect and adjust the weld, etc. The welding glass is of a limited size and is surrounded by an opaque material either in case of a hand shield or in case of a pivoted visor on a head shield. On head shields or welding helmets there is usually provided above the welding glass a so-called sight glass, i.e., a completely clear transparent glass, and this provides the further disadvantage that persons with bifocal glasses will have difficulties in observing the weld through a proper field of view of the glasses when they look through the sight glass. Accordingly, it is necessary for the welder to move away from time to time the visor in order to be able to obtain a good view when necessary working operations are to be performed and the welding arc is extinguished, which is uncomfortable and tiring, the working efficiency at the same time being reduced as a consequence thereof.

In order to eliminate the related drawbacks and thus gain precision, security and time when welding work is being performed, and above all in order to achieve this by providing a head shield which is more versatile and which is lighter and airier than the conventional "black mask" it has been proposed according to U.S. Pat. No. 3,868,727 a welding shield of the kind referred to above, wherein the dark welding glass as a locally defined curved portion of the welding shield, to be positioned in front of the eyes, at the sides and the bottom thereof is bounded by a curved transparent portion of lighter shade than the welding glass.

While the welder well protected can observe the welding operation through the dark welding glass, he has also the possibility to look laterally of and below the dark welding glass when the welding arc is extinguished, such that he has a sufficient view for performing such working operations as ignition of the electrode, knocking off slag, inspecting and adjusting the weld, exchanging the electrode, re-arranging welding clamps, using a grinding tool, etc. Moreover, the welder can easily observe predrilled spot welds and find tools which he has put away. Bifocal glasses can be used in a proper manner, which provides a correct concept of space and makes easier to estimate distances. Altogether, this means that increased safety at welding operations will be obtained, particularly in narrow spaces.

The object of the invention is to provide a welding shield of said latter type which further improves the comfort and safety at the welding, and this is achieved by providing a welding shield adapted to be located in front of the face of the welder for protection against harmful radiation and including a dark welding glass which forms a locally defined portion of the welding shield to be positioned in front of the eyes, characterized in that said welding glass is attached to a highly light-reflecting and UV-absorbing transparent planar panel surrounding the welding glass.

By a welding shield of the invention substantially all harmful UV radiation (ultraviolet radiation) is prevented from reaching the face of the welder, the reflected light at the same time serving to illuminate the region wherein the welding is performed, without harmful UV radiation simultaneously being reflected back towards the hands and causing serious injuries to them.

Additional objects and advantages of the invention in part will be set forth in the description which follows and in part will be obvious from the description or may be learned by practice of the invention.

The accompanying drawings which are incorporated in and constitute a part of this specification illustrate embodiments of the invention and together with the description serve to explain the principles of the invention.

Figures 1, 2:
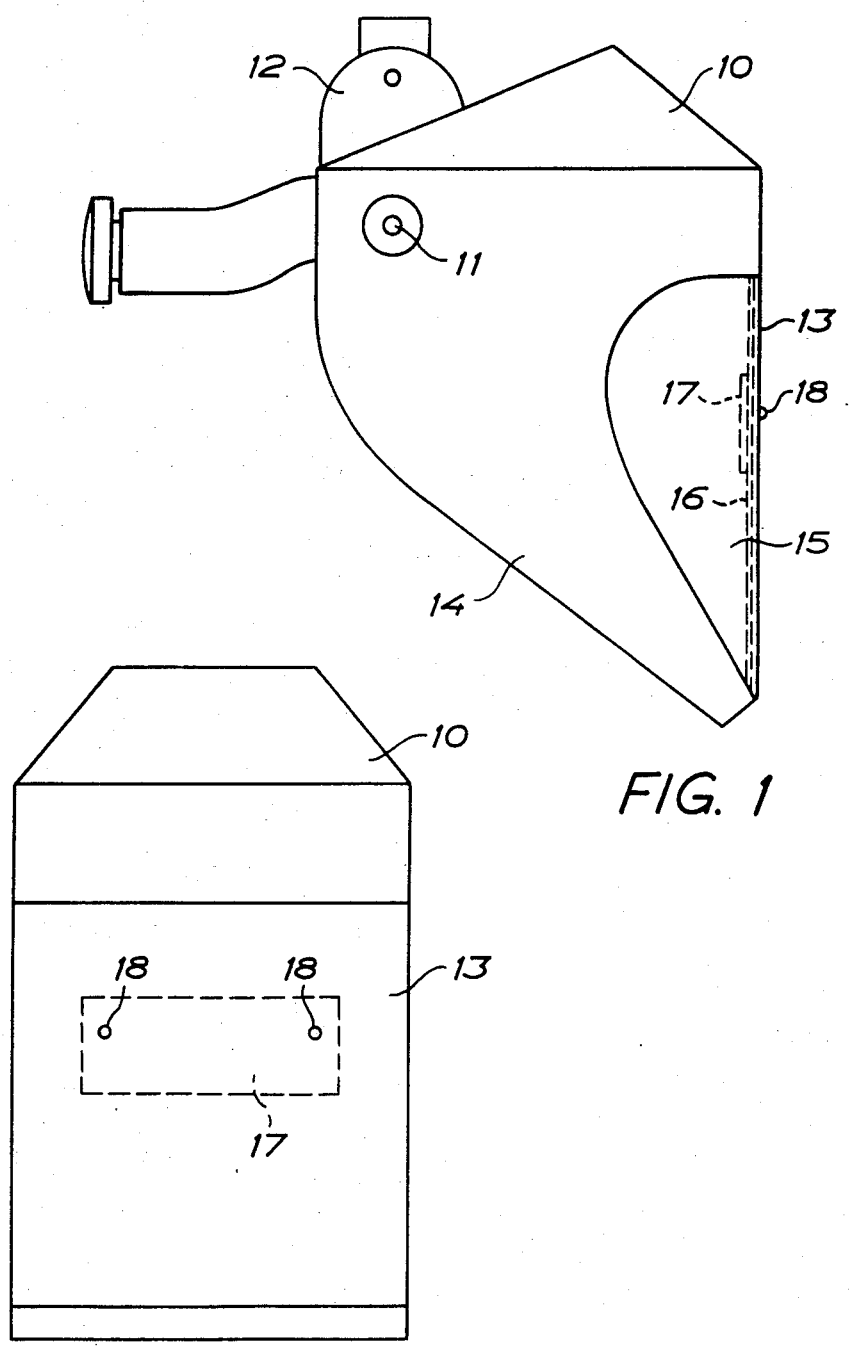
FIG. 1 is a side view of a head shield or welding helmet of the invention.
FIG. 2 is a front view of the head shield.
Figure 3:
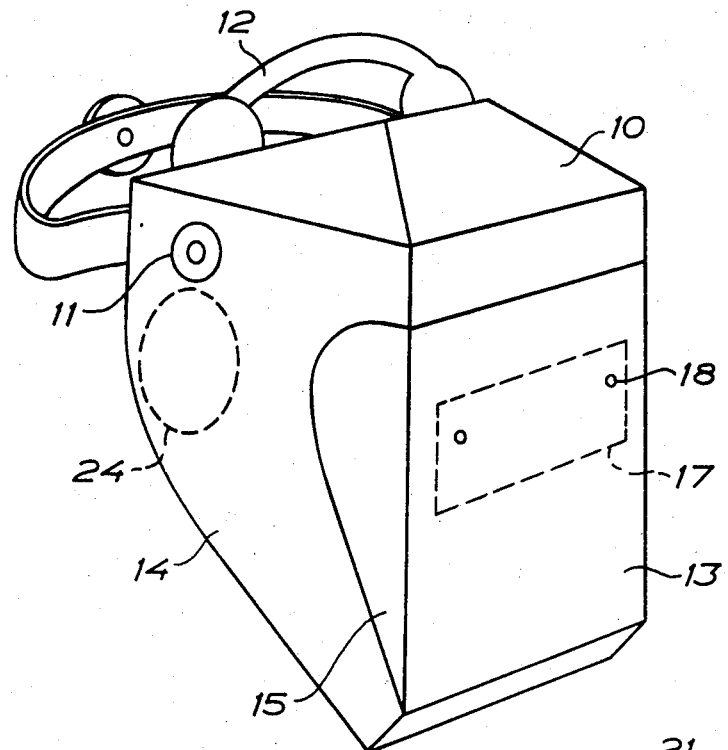
FIG. 3 is a perspective view of the head shield.

Reference will now be made in detail to the present preferred embodiments of the invention, examples of which are illustrated in the accompanying drawings.

The head shield shown in the drawings comprises an opaque cap portion 10 which is pivoted at 11 to a head gear 12 adapted to be located on the welder's head for supporting the head shield in a proper position as a visor in front of the welder's face. The head gear can be adjusted to different head shapes and sizes and can be of any conventional construction. The head shield has a planar front wall 13 and planar side walls 14. The front wall 13 and joining portions 15 of the side walls are made of a limped UV-absorbing material to be transparent. Suitable materials providing a particularly high absorption of UV radiation are such materials as are used for protective filters in the optical industry, and according to available technical data from the manufacturers provide practically 100 percent absorption within all UV wave lengths. Examples of such materials are UV absorbing MAKROLON 281 from Röhm GmbH Chemische Fabrik, Darmstadt, Federal Republic of Germany. The front wall 13 and the portions 15 can comprise interconnected panels of said material which are attached to the remaining part of the head shield, which may consist of another opaque material. The front wall 13 and the portions 15 can form a unit which is detachably secured to the cap portion 10 in order to be easily exchanged such that different types of units can be used for different welding currents. The entire head shield may also be made of the UV absorbing material as an injection molded or vacuum molded unit, the opacity of all portions except the front wall 13 and the portions 15 being obtained by a suitable coating, colouring or bifoliating.

Figures 4, 5:
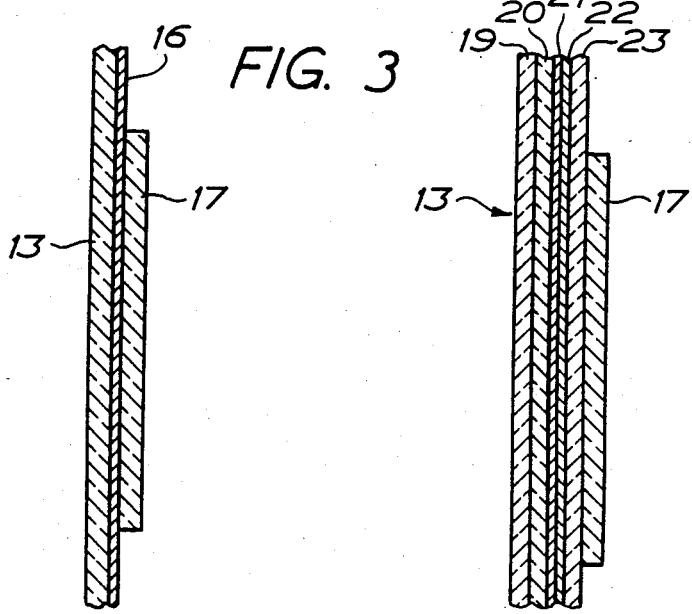
FIG. 4 is an enlarged fragmentary cross-sectional view of the welding shield proper.
FIG. 5 is a view similar to that of FIG. 4 of another embodiment of the welding shield.

The front wall 13 and the portions 15 are bifoliated on the inner side thereof with a bright silver layer 16, FIG. 4, which according to information from the manufacturer reflects 80 to 85 percent of incident visible light but does not significantly interfere with the welder's view through the head shield. The layer 16 can be applied as a foil or can comprise a layer which has been applied in another manner e.g. chemically.

Preferably, a brown black transparent foil having a thickness of one or two hundredths millimeters is applied to the inner side of the layer 16 in order to exclude UV radiation. This foil can have a lighter or darker shade depending on the welding current for which the shield is to be used.

A rectangular welding glass 17 is attached to the inner side of the planar front wall 13 to be located at the same level as the eyes of the person using the head shield. The welding glass can be attached by means of fasteners 18 which pass through unsymmetrically located apertures in the welding glass such that some adjustment of the vertical position of the welding glass on the front wall can be obtained by turning the welding glass around. E.g. the welding glass can be located in the upper position for a person using bifocal glasses.

FIG. 5 shows a preferred construction of the front wall 13 and the portions 15. The outer side is to the left and the inner side to the right. Then, from the left to the right there are two limped MAKROLON layers 19 and 20 which absorb UV radiation. A layer 21 follows which is light-reflecting and comprises a TEMPCON sun protection film type Silver-20 R which can be obtained from Svahns, Jonstorp, Sweden. Then, there is an absorbing coloured layer 22 comprising a TEMPCON sun protection film type Brons-25 NR, and finally there is on the inner side an absorbing MAKROLON layer 23 which forms also a protective layer so as to protect the films 21 and 22 from damage.

Visible light and UV radiation inciding towards a panel of the construction shown in FIG. 5 passes through the layers 19 and 20 in which UV radiation will be absorbed. 85 to 90 percent of the visible light will be reflected at the layer 21 which reflects also remaining UV radiation, if any. Such radiation will be absorbed on its way back when passing through the layers 19 and 20 such that in reality visible light only will be reflected towards the welding site. Tests which have been made with the construction according to FIG. 5 have shown that the transmission of UV radiation through the front wall 13 around the welding glass 17 is below 0.0001 percent while the Swedish Board of Occupational Safety and Health mentions 0.003 percent as the upper acceptable limit.

The head shield can of course be shaped in another way than that shown herein. However, it is preferred that the planar UV absorbing and light-reflecting front wall 13 is made large, because there is then automatically obtained an excellent working light independent of the general illumination in the premises wherein the head shield is being used. Due to the fact that the intense light of the welding arc is reflected towards the work piece, the contrast will be counterbalanced and there will be obtained a very good lead. The planar front wall can be easily wiped off and kept clean and can be combined in a simple manner with a supplementary glass (so-called 1000 hours glass) protecting against scattering. Moreover, the planar front wall makes possible a greater optical flatness such that "seasickness" of the user of the head shield will be avoided.

The side portions 15 can be made larger or smaller in order to allow lateral orientation but should not be made so large that too much light will be received inside the shield, because inside reflections will be obtained as a consequence thereof. In order to prevent as much as possible light from penetrating into the head shield from the back side thereof, which causes reflections of the type mentioned, the side portions 14 should have a large extension backwards and also should be mat black on the inside thereof.

On the inside of the side portions 14 there can be arranged ear protectors 24 for use of the head shield at grinding, slag knocking and other operations causing a high noise level.

The invention can be applied not only to head shields, which is, however, the most attractive application, but also to hand shields adapted to be held at one hand, or shields which are mounted on an adjustable support.

Essential according to the invention is that there is a free view around the conventional welding glass and that the intense light from the welding arc by reflection from the front side of the welding shield is used as working light while the harmful UV radiation is being absorbed.

It will be apparent to those skilled in the art that various modifications and variations could be made in the welding shield described without departing from the scope and spirit of the invention.

I claim:

1. Welding shield adapted to be located in front of the face of the welder for protection against harmful radiation, comprising a dark welding glass, a highly light-reflecting layer and a UV-absorbing layer together forming a transparent planar panel which extends beyond the top, bottom and side edges of the welding glass, and means mounting the welding glass to the backside surface of said panel, said welding glass forming a locally defined portion of the welding shield to be positioned in front of the eyes, surrounded by said panel.

2. Welding shield as claimed in claim 1 wherein said highly light-reflecting layer is innermost and a UV-absorbing layer is outermost.

3. Welding shield as claimed in claim 2 wherein the light-reflecting layer comprises a layer of bright silver.

4. Welding shield as claimed in claim 1 wherein the planar transparent panel is provided with a further coloured layer on the inside thereof.

5. Welding shield as claimed in claim 4 wherein the layer comprises a foil.

6. Welding shield as claimed in claim 1 wherein the welding glass is attached to the inner side of the planar transparent panel.

7. Welding shield as claimed in claim 1 arranged as the front wall of a head shield.

8. Welding shield as claimed in claim 1 including transparent highly reflective and UV-absorbing side portions which adjoin the front wall.

* * * * *